United States Patent [19]
Raskin et al.

[11] Patent Number: 5,364,451
[45] Date of Patent: Nov. 15, 1994

[54] PHYTOREMEDIATION OF METALS

[75] Inventors: Ilya Raskin, Manalapan; Nanda P. B. A. Kumar, New Brunswick; Slavik Douchenkov, East Brunswick, all of N.J.

[73] Assignee: PhytoTech, Inc., Morristown, N.J.

[21] Appl. No.: 73,258

[22] Filed: Jun. 4, 1993

[51] Int. Cl.$^5$ ............................ C21B 9/00; C22B 9/00
[52] U.S. Cl. ............................................. 75/710; 71/9;
210/602; 210/682; 210/688
[58] Field of Search ................ 75/710; 210/602, 682, 210/688; 71/9

[56] References Cited

U.S. PATENT DOCUMENTS

| | | | |
|---|---|---|---|
| 4,293,333 | 10/1981 | Drobot | 210/682 |
| 4,293,334 | 10/1981 | Drobot et al. | 210/685 |
| 4,732,681 | 3/1988 | Galun et al. | 210/611 |
| 4,872,985 | 10/1989 | Dinges | 210/602 |
| 4,904,386 | 2/1990 | Kickuth | 210/602 |
| 5,000,852 | 3/1991 | Tel-Or et al. | 210/602 |
| 5,100,455 | 3/1992 | Pinckard et al. | 71/9 |
| 5,120,441 | 6/1992 | Jackson et al. | 210/602 |

OTHER PUBLICATIONS

R. R. Brooks, Biological Methods of Prospecting for Minerals (John Wiley & Sons 1983).
Vegetables, The American Horticultural Society Illustrated Encyclopedia of Gardening, p. 112 (1974).
A. J. M. Baker, et al., "The Potential for the Use of Metal-Accumulating Plants for the *In Situ* Decontamination of Metal-Polluted Soils"; Sep., 1992, *Proc. EUROSOL Conf., European Conf. on Integrated Research for Soil and Sediment Protection and Remediation; MECC Maastricht, The Netherlands.*

*Primary Examiner*—Peter D. Rosenberg
*Attorney, Agent, or Firm*—Choate, Hall & Stewart

[57] ABSTRACT

A process for removal of metal ions from soil and methods for effecting such removal are described. The process is based on the growth of crop and crop-related members of the plant family Brassicaceae in metal-containing soils. These particular plants will absorb metals into their roots making them not leachable from the soils or will absorb the metal into their roots and transfer them to the shoots which can be easily harvested.

15 Claims, 1 Drawing Sheet

5,364,451

PHYTOREMEDIATION OF METALS

The invention was made with government support under Grant No. R818619-01-0 awarded by the Environmental Protection Agency to Rutgers, the State University of New Jersey. The government has certain rights in the invention.

BACKGROUND OF THE INVENTION

Deposition of metal-rich mine tailings, metal smelting, leather tanning, electroplating, emissions from gas exhausts, energy and fuel production, downwash from powerlines, intensive agriculture and sludge dumping are the most important human activities which contaminate soil systems with large amounts of toxic metals. The list of sites contaminated with toxic metals grows larger every year, presenting a serious health problem and a formidable danger to the environment.

In spite of the growing number of metal-contaminated soil sites, the costly process of removing and burying metal-contaminated soils, or isolating the contaminated sites, remain the most commonly used methods for reclaiming metal-contaminated soils.

SUMMARY OF THE INVENTION

The present invention pertains to a method of removing an amount of metal from a metal-containing soil environment using a plant of the family Brassicaceae. The method includes contacting at least one member of this plant family with the metal-containing soil environment and maintaining the member in the soil environment under conditions sufficient for the member to accumulate an amount of metal from the soil. In preferred methods, the plant is maintained in the soil for a time and under conditions sufficient for the plant to accumulate the metal shoots and/or roots. The shoot may be further harvested from the soil and disposed of.

The preferred methods of the invention utilize crop and/or crop-related members of the family Brassicaceae, especially the Brassiceae tribe. Preferred Brassiceae include the mustards and related species. These plants concentrate metals in roots and transport the metals to the above ground shoots which can be easily harvested.

The crop and/or crop-related members of the plants used in the present invention can accumulate metals between 30 to about 1000-fold over metal concentrations in soil. This accumulation is equivalent to a metal content of about 30% of the dry weight in the plant root and up to about 3.5% of the dry weight of the plant shoot.

The metal can include stable or radioactive isotopes of, for example, mercury, cadmium, cobalt, nickel, molybdenum, copper, arsenic, selenium, zinc, antimony, beryllium, gold, barium, manganese, silver, thallium, tin, rubidium, strontium, yttrium, technecium, ruthenium, palladium, indium, vanadium, cesium, uranium, plutonium, and cerium. In the preferred methods of the invention, the metal includes lead and chromium.

This invention also pertains to crop and/or crop-related members of the family Brassicaceae and members of the tribe Brassiceae which can accumulate metals from a metal-containing soil environment. Preferred members include *Brassica juncea* and particularly preferred members include *B. juncea* cultivars 426308 and 211000. These Brassica cultivars are capable of accumulating a total of between about 2% and 3.5% of their shoots on a dry weight basis as lead, and between 10% and 30% of their roots on a dry weight basis as lead.

The invention also relates to a crop and/or crop-related member of the family Brassicaceae comprising between about 2% to about 30% dry weight as lead. Preferably, this crop-related member contains the metal in a shoot portion of the plant. Preferred plant members are Brassica species selected from the group consisting of *B. juncea* and *B. oleracea*.

Cultivation of the metal-accumulating plants described herein can reduce the concentration of radioactive and non-radioactive toxic metals in soils to environmentally acceptable levels. Crop and/or crop-related members of the plants of the present invention are suitable precisely because of their high biomass production and adaptability to growth using well-established agricultural practices for high-density monoculture cultivation under a wide variety of climatic conditions.

DETAILED DESCRIPTION OF THE INVENTION

Figure 1A:
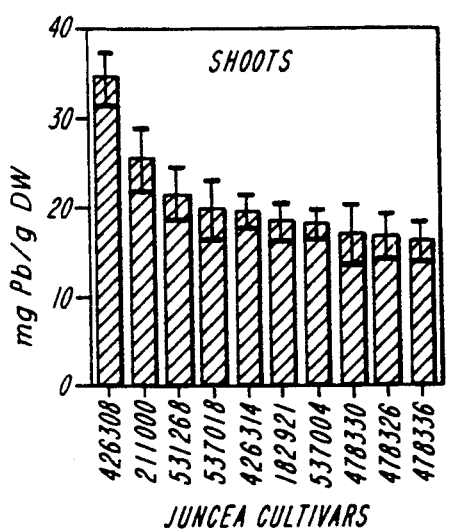
FIG. 1 is a bar graph illustrating accumulation of lead by *Brassica juncea* cultivars in shoots (FIG. 1A) and roots (FIG. 1B).

One aspect of the present invention is a method for removing metals from metal-contaminated soil using metal-accumulating crop plants. In this context, metal "accumulating" plants refers to the ability of the plants described herein to perform one, or more, of the following activities: (i) transporting metal from soil particles and/or soil liquid into roots; (ii) physical and/or chemical sorption of metal to the root biomass; (iii) prevention or inhibition of leaching of the metal from the soil environment.

The preferred plants used in the present method are members of the plant family Brassicaceae. Members of this family include, but are not limited to, cabbages, mustards and radishes. The most preferred members of this family belong to the tribe Brassiceae. Members of this tribe include mustards of the genus Brassica and related species, described in more detail below.

A key aspect of the present invention is that the preferred method relies upon use of crop and/or crop-related members of the above-identified family and tribe. The term "crop member" refers specifically to species of the genus Brassica which are commercially grown as sources for vegetables, oilseeds, forage, fodder and condiments. Examples of crop members of the family Brassicaceae include, but are not limited to, digenomic tetraploids such as *Brassica juncea* (L,.) Czern. (mustard), *B. carinata* Braun (ethopian mustard), and *B. napus* (L.) (rapeseed); and monogenomic diploids such as *B. oleracea* (L.) (cole crops), *B. nigra* (L.) Koch (black mustard). and *B. campestris* (L.) (turnip rape).

"Crop-related" members are those plants which have potential value as a crop and as donors of agronomically useful genes to crop members. Thus, crop-related members are able to exchange genetic material with crop members, thus permitting breeders to effect interspecific (i.e., from one species to another) and intergeneric (i.e., from one genus to another) gene transfer. "Crop-related" members include *Raphanus sativus* (L.) (radish), *Sinapis alba* (L.) (white mustard). *S. arvensis* (L.), *S. flexuosa* Poiret and *S. pubescens* (L.). Those having ordinary skill in the art will understand that methods of exchanging genetic material between plants and testing effects of interspecific and intergeneric gene transfer are well characterized. See, for example Goodman et al., Science, 236: 48–54, 1987, incorporated herein by reference. Thus, "crop-related" members not presently identified, or suspected of removing metal, can be identified using no more than routine experimentation.

Unless indicated otherwise, "crop and/or crop-related" members will be referred to collectively as "members".

The members used in the present invention are plants that: (a) can be grown to high biomass; (b) are adaptable for growth in various agroclimatic conditions; (c) are adaptable to well-established agricultural practices for high-density monoculture; (d) are amenable to genetic manipulation by mutagenesis and/or gene transfer; (e) can produce several crops per year; and (f) are related to known wild plants which do accumulate metals.

Preferred plant members used in the present invention should therefore be contrasted to "wild" or non-crop and/or non-crop-related members; i.e., those species that are endemic to metal-containing soils in scattered areas of the world. These wild members are not amenable to large scale agricultural practices and they normally have very low rates of germination and biomass accumulation in the laboratory and in the field. Levels of metal accumulation in these non crop-related members can be several percent metal on a dry weight basis. See, Reeves and Brooks, $Environ.\ Poll.$, 31: 277 (1983); Baker et al., $Taxon$, 34:89 (1985).

Examples of non-crop-related members of the family Brassicaceae are members of the genus Alyssum found on serpentine soils in southern Europe and Thlaspi from calamine soils throughout Europe. In particular, non-crop-related members of this family include $T.\ caerulescens$ Whitesike Mine, $A.\ tenium$, $A.\ lesbiacum$, $A.\ murale$ and $A.\ ochroleucum$ (see also Baker, et al., $Biorecovery$ 1:81–126 (1989)).

The members used in the present methods also include mutagenized and/or genetically engineered plants. For example, ethylmethylsulfonate (EMS) is a potent mutagen which increases genetic variability by increasing the frequency of genomic mutations. See, for example, Redei, G. P. "Genetic Manipulations of Higher Plants", L. Ledoux (ed), Plenum Press, N.Y., 1975. Ethylmethylsulfonate has been used in selection programs to produce heritable changes in plant biochemistry and physiology, particularly in $Axabidopsis\ thaliana$, a member of the Brassicaceae.

A screening system described below in Example 1 is used to identify terrestrial plant species with the highest metal accumulating potential (i.e. metal content of dried plant residue/metal content of growth medium). The seeds of these self-pollinating lines are then subjected to EMS mutagenesis using, for example, the methods of Estell et al, "The mutants of Arabidopsis", p. 89 in $Trends\ in\ Genetics$, Elsevier Science Publishers, B.V., Amsterdam, 1986. (See Example 2).

Briefly, mutagenesis is accomplished by soaking dry seeds in EMS solution at room temperature. The EMS induces heterozygous mutations in those cells which will produce the reproductive structures. The M1 generation of plants is allowed to self-fertilize and at least 50,000 seedlings of the M2 progeny are screened for metal tolerance in artificial aqueous solutions containing various metal concentrations. The most tolerant M2 plants, those growing most vigorously, are analyzed for accumulation of metals.

Furthermore, the terrestrial plants used in the methods of the present invention can be genetically manipulated using well-established techniques for gene transfer. It is well-known that a variety of non-photosynthetic organisms respond to metals by production of metallothioneins (MT's), low molecular weight proteins encoded by structural genes. See, for example G. Maroni, "Animal Metallothioneins," pp. 215–232 in $Heavy\ Metal\ Tolerance\ in\ Plants:\ Evolutionary\ Aspects$, (ed. A. J. Shaw), CRC Press, Inc., Florida, (1990). The present invention contemplates increasing root uptake of metals by heterologous expression of MT's in transgenic plants.

A mammalian MT cDNA (e.g. monkey) can be obtained commercially or from an established source and a restriction enzyme fragment cloned into, for example, an Agrobacterium-based plant transformation/expression vector such as pJB90, a derivative of pGSFR780A. See, De Block et al, $Physiol.\ Plant.$ 91: 694–701 (1989).

Seedling segments of terrestrial plants used in the present method are then incubated in the presence of a suspension of bacterial cells (e.g. $Agrobacterium\ tumefacieus$) carrying the expression vector. After several days, the regenerating seedling segments are transferred to the appropriate selection medium and further incubated. This results in transformants containing the mammalian MT genome (see Example 5).

The transformants are analyzed for the presence of MT DNA by Southern and Northern hybridization using mammalian MT as the probe. The transformants are also analyzed for expression of MT protein by immunoblot analysis with antisera against the mammalian MT. See established protocols of, for example, Sambrook et al. (1989) Molecular Cloning: A Laboratory Manual, Cold Spring Harbor Laboratory Press, N.Y.

The preferred methods of the invention involve growing one more members of these plants under conditions sufficient for them to accumulate metal in their biomass. The term "metal" preferably refers to metal ions that are found in the metal containing environment. It will be appreciated that this term will also include elemental metal that is not in an ionic form.

The metals that can be accumulated according to the method of the present invention include stable metals and radioactive metals such as lead, chromium, mercury, cadmium, cobalt, barium, nickel, molybdenum, copper, arsenic, selenium, zinc, antimony, beryllium, gold, manganese, silver, thallium, tin, rubidium, vanadium, strontium, yttrium, technecium, ruthenium, palladium, indium, cesium, uranium, plutonium, and cerium. The term "metal" is also intended to include more than one metal since plants may concentrate several different metals, implying that the mechanism of metal uptake is not always metal specific. The term "metal" also includes mixtures of metals and common organic pollutants such as, for example, lead or chromium in combination with nitrophenol, benzene, and/or alkyl benzyl sulfonates (detergents).

The metal-containing environment into which these plants are introduced is not intended to limit the scope of the invention. That is, as long as the environment can sustain growth of members of the family Brassicaceae, the metal-containing environment can range from purely aquatic environments (i.e., hydroponic culture) to soil environments of varying degrees of water saturation, organic matter content, mineral content, and the like. It will be appreciated by those of ordinary skill in the art that the term "soil" can, therefore, include a wide variety of chemical and physical types.

The metal-accumulating members suitable for the present methods will extract metal from the environment into the roots of the plant. Preferably, the plants will translocate the metals from the roots into the shoots (i.e., the above ground portions of the plant). The rates of accumulation of metal can vary depending on a variety of factors, including the ratio of soluble and insoluble metal in the soil, the total metal concentration, soil type, pH, moisture content, organic matter content, soil temperature, planting density, and fertilizer use.

Generally, metal accumulation by the preferred members of the family Brassicaceae can be as high as 1000-fold above levels present in the soil. The most preferred plant members accumulate several percent of metal as dry weight of shoot biomass and up to 30% metal by weight in dried root biomass. Shoots or roots are routinely harvested for certain Brassica species, for example *B. campestris* and *Raphanus sativus*. The ability of the plants of the present invention to accumulate metal in the shoots is important because the shoots represent the harvestable (i.e., above ground) biomass. The accumulation of metal in the shoots is preferred because generally roots are more difficult to harvest than shoots when the plants are grown in soil.

The members of the family Brassicaceae of the present invention have undergone screening and selection procedures to yield several lines of fast growing metal-accumulating plants that can effectively remove radioactive and non-radioactive metals from artifactual and natural soils. These plants concentrate metals in roots and transport the metals to the above-ground shoots which can be easily harvested.

The screening procedures detailed in Example 1 can be applied to other members of the family Brassicaceae and other metal ions that are not described here. To measure metal accumulation of any plant in a metal-containing soil, seeds of the particular plant(s) to be tested are grown in a greenhouse, the appropriate metal is administered to the plant and soil, and the roots and shoots harvested for routine determination of biomass and metal content. Chemical analysis of metal content in soils and plants is well-characterized. See, for example, Blincoe et al., *Comm. Soil. Plant Anal.*, 18: 687 (1987); Baker, D. E. and Suhr, S. H., "Atomic Absorption Spectrometry", pp. 13–27 in *Methods of Soil Analysis*, part 2, *Am. Soc. Agron.*, Madison, Wis., (1982). Metal in plant tissues is preferably assayed with plasma spectrometry, allowing ashing and acid extraction. Metal remaining in the solution is measured by, for example, atomic absorption or plasma spectrometry. See, Soltanpour et al., "Optical emission spectrometry", pp. 29–65 in *Methods of Soil Analysis*, part 2, Am. Soc. Agron., Madison, Wis., (1982).

The methods of removing metal from soil using the presently described members involve contacting the soil with at least one member of the family Brassicaceae and maintaining the plant member under environmental conditions sufficient for the plant to accumulate metal from the metal-containing environment. Methods for maintaining the plant are known to those of ordinary skill in the art and include well-established agronomic practices for growing crop plants. See, for example, Chopra, V. L. and Prakash, S., (eds.) *Oilseed Brassicas in Indian Agriculture*, Vikas Publishing House Ltd., New Delhi, (1991); Downey, R. K. and Robbelen, G., "Brassica species", pp. 339–362 in Robbellen et al. (eds.), *Oil Crops of the World*, McGraw-Hill, New York, 1989.

At present, there are no known agronomic practices which would allow monocultural cultivation of wild, non-crop-related members of the family Brassicaceae. However, the members described in the present application herein are routinely grown under conditions of intensive, monocultural systems in many countries around the world. This is possible because of the availability of herbicides and pesticides registered for use with member brassicas along with information on seed treatment, sowing time, stand establishment and nutrition. In addition, the planting and harvesting of cultured, crop and/or crop-related brassicas can be mechanized providing a qualitative difference in the investment necessary for growing each crop.

The invention described herein will be illustrated by the following examples.

EXAMPLE 1

Screening Assay

The seeds of crop and/or crop-related species of selected members of the Brassicaceae are sown in a potting mix (Terralite ™ Metro-Mix ™; mfg. by Grace Fiera Horticultural Products Co., Milpetas, Calif.) and grown in a greenhouse equipped with supplementary lighting (16 h photoperiods; 24° C.). Seedlings are fertilized every two days with a full strength Hoagland's solution. After 10 days the seedlings are transplanted (two per 3.5 inch plastic pot) into an acid pre-washed 1:1 (v/v) mixture of coarse sand and coarse Perlite.

During a 7-day long period of establishment, seedlings are well-watered and fertilized with $KNO_3$ solution. Thereafter, aqueous solutions of lead in the form of $Pb(NO_3)_2$ or chromium in a form of $K_2Cr_2O_7$ are administered to the surface of the growing medium to obtain 625 ug $Pb^{+2}$ or 3.5 ug $Cr^{+6}$ per gm of dry soil. After the metal application, plants are irrigated with water only. Control plants are watered from the top with $KNO_3$ solution on the day of metal treatment to deliver the same amount of $NO_3^{-1}$ or $K^{+1}$ as the salts of metals. For all treatments the excess soil moisture is trapped in 4 inch plastic saucers placed below each pot. Roots and shoots of treated and control plants are harvested 12 to 20 days after the metal treatment. Metal content, dry matter accumulation, and metal-related toxicity in treated plants is determined and compared to the untreated control. Metal content of roots and shoots is measured by direct current plasma spectrometry.

In an interspecies screen summarized below, lead uptake by members of the Brassiceae tribe (*) was compared with non-Brassica plants and with each other (Table 1).

TABLE 1

Lead-accumulating capacities of different members of Brassiceae tribe (*). The experiment was repeated with similar results. Standard error did not exceed 30% of the mean. Lead content ($\mu$g $Pb^{+2}$/g dry weight).

| Plant | Tissue | Days after treatment | |
|---|---|---|---|
| | | 12 | 20 |
| *B. juncea* * | Shoot | 9,346 | 18,812 |
| | Root | 70,090 | 91,666 |
| *B. carinata* * | Shoot | 1,856 | 8,757 |
| | Root | 76,815 | 115,461 |
| *B. nigra* * | Shoot | 1,439 | 2,489 |
| | Root | 29,671 | 110,011 |
| *B. campestris* * | Shoot | 1,242 | 6,941 |

TABLE 1-continued

Lead-accumulating capacities of different members of Brassiceae tribe (*). The experiment was repeated with similar results. Standard error did not exceed 30% of the mean. Lead content ($\mu g$ $Pb^{+2}$/g dry weight).

| Plant | Tissue | Days after treatment 12 | Days after treatment 20 |
|---|---|---|---|
| | Root | 22,651 | 100,354 |
| B. oleracea* | Shoot | 2,333 | 1,416 |
| | Root | 51,420 | 51,399 |
| B. napus* | Shoot | 5,720 | 3,877 |
| | Root | 68,117 | 60,768 |
| Sinapis arvensis* | Shoot | — | 498 |
| | Root | — | 42,660 |
| Raphanus sativus* | Shoot | — | 886 |
| | Root | — | 44,157 |
| Nicotiana tabacum | Shoot | — | 786 |
| | Root | — | 24,872 |
| Sorghum bicolor | Shoot | — | 280 |
| | Root | — | 14,693 |
| Zea mays | Shoot | — | 236 |
| | Root | — | 8,165 |

Of all the species studied, Brassica juncea was the best accumulator of lead in shoots, accumulating lead 30-fold over soil values. B. carinata accumulated the highest levels of lead in roots, accumulating lead about 185-fold over soil values. In general, all species of brassicas accumulated exceptionally high levels of lead in shoots and roots. Other members of the Brassiceae tribe were also good accumulators of lead when compared to species belonging to different taxonomic groups. Over ninety percent of lead present in the shoots of B. juncea grown on lead-containing medium for 12 days was present in the stems and reproductive tissue. Leaves contained smaller amounts of lead on a dry weight basis.

In addition to having the highest accumulating ability in the shoot portions, B. juncea showed low lead toxicity. It is also known to be a high biomass producer (average yield of 18 tons/hectare: See, Bhargava, S. C., "Physiology", pp. 161–197 in *Oilseed brassicas in Indian Agriculture*, (eds. Chopra, V. L. and Prakashs, S.), Vikas Publishing House Ltd, New Delhi, (1991)).

EXAMPLE 2

EMS Mutagenesis

This example illustrates a protocol for use in mutagenizing plant members of the family Brassicaceae.

1. Dry seeds are placed in about 100 ml of a 0.3% (v/v) solution of EMS (obtained from Sigma chemicals, St. Louis, Mo.). There may be some variation from batch to batch of EMS so it may be necessary to adjust this concentration somewhat. Between 20,000 to 250,000 seeds are mutagenized at a time. Ethyl methane sulfonate (EMS) is a volatile mutagen. It should be handled only in a fume hood and all solutions and materials which it contacts should be properly disposed of.

2. Seeds are mixed occasionally or stirred on a stir plate and left at room temperature for 16–20 hours. The rate of mutagensis may be temperature-dependent so using a magnetic stir plate may alter the results by warming the solution.

3. Seeds are washed with distilled water 10 to 15 times over the course of 2 to 3 hours by decanting the solution, adding fresh water, mixing, allowing the seeds to settle, and decanting again. After about 8 washes the seeds are transferred to a new container and the original is disposed of.

4. After washing, the seeds are immediately sown at about 1 seed per square cm (3000 seeds in 50 ml of 0.1% agar per 35×28×9 cm flat).

5. After several weeks it is useful to estimate the number of seeds which have germinated in order to know the size of the M1 generation. About 75% of the mutagenized seeds usually germinate. Ideally, the M1 estimate is the number of plants which produce M2 seed, but this is much more difficult to measure.

6. Plants are grown until they begin to die naturally and are then allowed to dry completely before harvesting. Complete drying improves the yield and simplifies harvesting.

EXAMPLE 3

Selection of Brassica cultivars

Identification of B. juncea as the best shoot accumulator (see Example 1) allowed an exhaustive screening of 120 B. juncea cultivars hoping to utilize existing genetic variability and find the best metal-extracting cultivars. B. juncea cultivars originating from 4 different continents were obtained from Dr. Peter K. Bretting, USDA/ARS, Iowa State University, Ames, Iowa 50011. The screening methods described in Example 1 were used throughout. Seedlings were exposed to 625 micrograms lead per gram dry weight soil for 14 days.

Figure 1B:
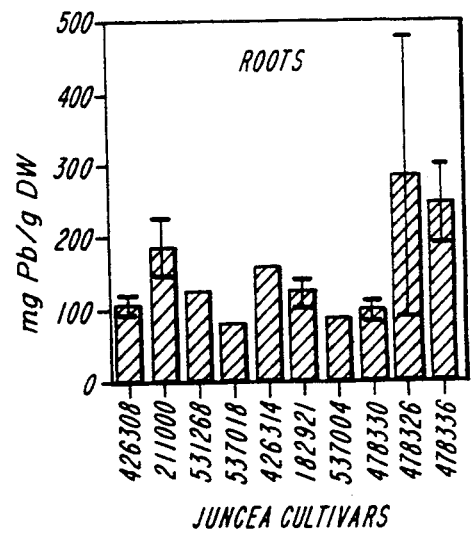

FIG. 1 demonstrates the ability of the ten best lead-accumulating cultivars of B. juncea identified in our screen to concentrate lead in shoots (A) and roots (B). Cultivar 426308, the best shoot accumulator identified so far, accumulated almost 55-fold lead in the dried shoots, a lead concentration of 3.5%. Moreover, roots of 426308 were able to concentrate lead 173-fold over the lead levels in the growing medium. This is equivalent to about 10% by weight of lead in the dried roots. The highest root accumulation was, however, observed in lines 211000, 478326 and 478336. These cultivars concentrated lead in their roots about 320-fold, 480-fold, and 350-fold, respectively, equivalent to about 20%, 30% and 25% by weight of lead in the dried roots. All lead-accumulating cultivars are vigorous plants with high biomass production—another important trait for a plant to be used for metal extraction.

In chemical engineering terms, Brassica juncea roots can perform chemical precipitation and are an extremely effective ion exchange resin and stabilize lead in the soil, as demonstrated below. Twelve day old seedlings of Brassica juncea cultivar 173874 are transplanted in groups of 15 plants each into 3.5" pots with a sand/Perlite mixture (150 g/pot by dry wt.), placed in 4.5" plastic saucers, and allowed to grow further for 20 days. At the same time, pots containing the same amounts of sand-Perlite mixtures but without plants are maintained as controls. Each pot (with and without plants) is watered on alternate days with 100 mL of tap water. In addition, 30 milliliters of full strength Hoagland nutrient solution are added weekly to each pot. At the end of the 20th day after transplanting, pots with and without plants are flushed with 10 volumes of tap water. Thereafter, the lead solution is administered into each pot to obtain the final lead concentration of 625 ppm in dry soil. Control pots and pots with plants are watered with tap water every other day.

Figure 2:
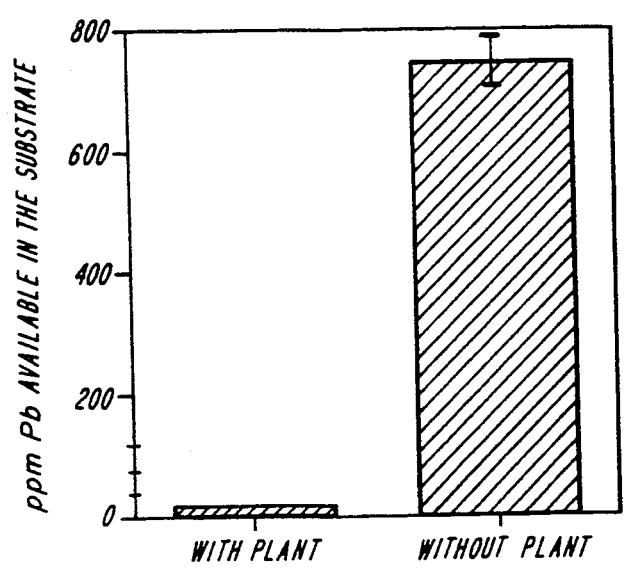
FIG. 2 is a bar graph illustrating stabilization of lead by *B. juncea*.

On the sixth day after lead treatment, 1 ml of solution leached from each pot into the plastic saucer is collected to determine the available lead by atomic absorption spectroscopy. As shown in FIG. 2, in the pots without plants, between about 700–800 ppm lead was measured in the leachate. In the pots with plants, less than 20 ppm lead was measured. The experiment indicates that *B. juncea* roots can effectively immobilize lead in soil, making the lead much more difficult to leach from the soil.

EXAMPLE 4

Accumulation of Chromium

Chromium is much more toxic to plants than lead. Eighteen micrograms $Cr^{+6}$/g DW soil, supplied for 20 days, were lethal for all tested Brassica species. Lethality is determined by observations of plant wilting and death by the end of the treatment. Tissue chromium is measured by plasma spectrometry following ashing and acid extraction. See Soltanpour et al, supra. However, at lower concentrations of $Cr^{+6}$ (about 3 to about 9 micrograins $Cr^{+6}$/g soil), crop-related brassicas are extremely good accumulators of this metal. In particular, both *B. juncea* and *B. oleracea* are excellent accumulators of $Cr^{+6}$ (Table 2). For example, *B. juncea* cultivar 21100 concentrated chromium in its roots 650-fold and in its shoots 90-fold. Therefore, the accumulating capacity for chromium in both shoots and roots of Brassicaceae species is even higher than for lead. *B. juncea* is likely better suited for chromium remediation than *B. olercea* because of its higher biomass production and ease of cultivation. To our knowledge, the above experiments are the first conclusive demonstration of the ability of any plant to accumulate chromium.

TABLE 2

Phytoremediation capacities of *B. oleracea* and *B. juncea* exposed to 3.5 and 8.5 μg $Cr^{+6}$/g dry soil for 20 d. Chromium content is expressed as microgram total $Cr^{+6}$/g dry weight tissue.

| Plant | Tissue | μg $Cr^{+6}$/g tissue 3.5 | 8.5 |
|---|---|---|---|
| *B. oleracea* | Shoot | — | 3 ± 53 |
| | Root | — | 2578 ± 204 |
| *B. juncea cultivars:* | | | |
| Rcb J* | Shoot | — | 398 ± 43 |
| | Root | — | 1705 ± 136 |
| 182921 | Shoot | 226 ± 64 | |
| | Root | 1834 ± 35 | |
| 211000 | Shoot | 334 ± 112 | |
| | Root | 2265 ± 239 | |
| 173874 | Shoot | 182 ± 81 | |
| | Root | 1945 ± 7 | |

*Rcb J - obtained from Crucifer Genetics Cooperative, Madison, WI.

EXAMPLE 5

Vector Construction and Transformation of *B. juncea* with MT Genes

A. Vector Construction

Monkey MT cDNAs (MT1 & MT2) are obtained from Dr. Dean H. Hamer, National Institutes of Health, Bethesda, Md. A 341 bp Hind III/Bam HI fragment containing the entire MT1 coding sequence including the initiator methionine codon is cloned into the Hind III/Bgl II site of pJB90 to give plasmid pNK1. pJB90, a derivative of pGSFR780A (a gift from Dr. Deepak Pental, Tata Energy Research Institute, New Delhi, India) is an Agrobacterium based binary, plant transformation/expression vector. This plasmid contains a plant selectable hpt (hygromycin phosphotransferase) gene and a multiple cloning site for the insertion of foreign DNA, between the T-DNA border repeats. The plasmid also contains a gene for spectinomycin resistance, functional in bacterial cells. pNK1 propagated in *E. coli* Dh5 was used to transform *Agrobacterium tumefaciens* strain pGV2260 (Deblaere et al., *Nucl-Acids Res.*, 13:4777 1985) by the freeze-thaw method (Ebert et al., *PNAS, U.S.A.*, 84:5745 1987).

B. Transformation of *B. juncea*

The 10 best hyperaccumulating *B. juncea* lines—173874, 182921, 211000, 250133, 426314, 426308, 531268, 537004, 537018—were selected for transformation.

*Agrobacterium tumefaciens* strain pGV2260 carrying pNK1 is grown overnight (220 rpm, 28° C. in dark) in 5 mL of liquid YEB (0.5% beef extract; 0.1% yeast extract; 0.5% peptone; 0.5% sucrose; 0.005% $MgSO_4.7H_2O$ in distilled water) containing 100 mg/L each of spectinomycin and rifampicin. One mL of this suspension is used to inoculate 50 mL of the YEB with the same concentrations of antibiotics and allowed to grow overnight. On the third day, the bacteria are harvested by centrifugation (5500 rpm) and resuspended in filter sterilized liquid MS (see Murashige, T., and Skoog, F., *Physiol. Plant*, 15: 473–497 (1962)) modified medium (MS salts & vitamins with 10 g/L each of sucrose, glucose and mannitol) supplemented with 200 micromolar acetosyringone and 100 mg/L each of spectinomycin and rifampicin at pH 5.6 The optical density of the bacterial suspension is adjusted to about $A_{600}=1.0$ and the bacteria grown for 6 hours, harvested as before are resuspended in the same medium. Freshly cut hypocotyl explants are incubated in the bacterial suspension for 1 h and co-cultivated on MS modified medium supplemented with 2 mg/L BAP (6-benzylaminopurine) and 0.1 mg/L NAA (naphthaleneacetic acid). After 2 days the explants are transferred to MS medium supplemented with 2 mg/L BAP, 0.1 mg/L 2,4-D (2-4 dichlorophenoxyacetic acid), 200 mg/L Cefotaxime and 30 micromolar $Ag(NO_3)_2$ and 10 mg/L Hygromycin B. After 10 days incubation on this medium, the explants are shifted to MS supplemented with 2 mg/LBAP, 0.1 mg/L NAA, 200 mg/L Cefotaxime, 10 mg/L Hygromycin B and 10% coconut milk. Shoots developed in 15–20 days are grown further and rooted in the presence of 20 mg/L hygromycin. We have obtained transformants with the line 173874 at a frequency of about 2%.

C. Characterization of MT gene expression in transgenic plant lines

About 15 independent transgenic plants are generated for each *B. juncea* line mentioned above. The putative transformants are analyzed for the presence of MT1 DNA by Southern and Northern hybridization analysis using MT1 cDNA as a probe. The putative transformants are analyzed for expression of MT1 protein by immunoblot analysis with antisera against monkey MT.

Transgenic lines expressing high MT levels are selected and tested for lead and chromium accumulation and metal tolerance in greenhouse trials described above. The transgenic lines are evaluated in large scale greenhouse trials which will utilize lead and chromium contaminated soil collected from the polluted sites.

Conclusions

The plant members described in the present invention represent a dramatic improvement in the ability to accumulate metals because of their much higher total biomass accumulation than wild, non-crop-related members of the Brassicaceae described in the literature. For example, *B. juncea* on an average yields 18 tons/hectare of harvestable biomass (Bhargava, S. C., supra). This is an order of magnitude higher than can be expected from the wild, non crop-related species of the Brassicaceae grown under the most favorable conditions.

Based on the available information, the following calculation of the rate of lead removal from contaminated soils can be made. Assuming total above-ground biomass production of 10 tons/hectare and 3.5% (dry weight) lead accumulation in plant shoots, one planting of the best lead-accumulating lines of *Brassica juncea* (cultivar 426308) can remove as much as 350 kg lead/hectare. In most of the areas of the United States, 3 sequential crops of this plant can be grown each year. Therefore, the best metal-accumulating lines of crop brassicas selected according to the methods of the present invention can extract one ton of lead per hectare per year. These estimates of the metal-removing capabilities of crop-related plants of the present invention assume that the soils can be extracted to a depth of up to one meter, which approximates the depth to which the roots of crop-related members of the family Brassicaceae can reach under favorable conditions.

The most commonly used method for cleaning toxic metal-contaminated soil is removal and isolation which costs an average of about $400 per ton of soil. If the contamination is 80 cm deep in sandy loam soil having a density of about 2.0 grams/cm., it will cost about $2.56 million to clean up one acre using this soil removal method.

The cost of growing the crop-related members of the Family Brassicaceae in the present invention may be approximated from the cost of alfalfa production in New Jersey which is about $320.00 per acre for the average farmer. Approximately 4.2 tons of dry plant matter per acre can be reduced to 40 kilograms of ash per acre if the plants are incinerated. Removing and burying that much plant residue will cost from about $640 to about $1,680 per acre, making the total cost of one crop between $960 and $2,000. Therefore, growing even ten sequential crops of the plants described in the present invention will be several orders of magnitude cheaper than a soil removal method. Furthermore, this method is better for the environment since it reclaims the soil making it usable rather than permanently disposing of the soil.

Under some circumstances, the metal can actually be reclaimed from the highly enriched plant ash. This will completely eliminate the need for residue burial and provide a truly environmentally friendly remediation technology.

Equivalents

It should be understood that various changes and modifications of the preferred embodiments may be made within the scope of the invention. Thus it is intended that all matter contained in the above description be interpreted in an illustrative and not limited sense.

We claim:

1. A method of removing an amount of metal from a metal-containing soil environment, comprising:
   identifying a metal-containing soil environment;
   altering metal uptake capability of members of the family Brassicaceae by transforming said members with a vector containing a cDNA sequence encoding metallothionein;
   screening a plurality of said altered members of the family Brassicaceae for at least one altered member having an ability to accumulate metal in shoots thereof;
   maintaining said at least one altered member in said metal containing soil environment under conditions sufficient for said at least one altered member to accumulate said metal from said metal containing soil environment.

2. The method of claim 1, wherein the step of altering comprises altering crop members of the family Brassicaceae.

3. The method claim 1, wherein the step of altering comprises altering crop-related members of the family Brassicaceae.

4. The method of claim 2, wherein the crop member is selected from the group consisting of *Brassica juncea* and *Brassica oleracea*.

5. The method of claim 3, wherein the crop-related member is selected from the group consisting of *Raphanus sativus* (L.) (radish), *Sinapis alba* (L.) (white mustard). *S. arvensis* (L.), *S. flexuosa* Poiret and *S. pubescens* (L.).

6. The method of claim 1, wherein the step of screening comprises screening a plurality of altered members of the family Brassicaceae for at least one altered member having an ability to accumulate at least about 10% of metal in roots on a dry weight basis.

7. The method of claim 1, wherein the step of screening comprises screening a plurality of altered members of the family Brassicaceae for at least one altered men, her having an ability to accumulate at least about 2% of metal in shoots on a dry weight basis.

8. The method of claim 1, wherein the metal is selected from the group consisting of lead and chromium.

9. The method of claim 1, further comprising harvesting said at least one altered member from said soil environment.

10. A method of removing an amount of lead or chromium from a lead or chromium-containing soil environment, comprising:
    altering metal uptake capability of a member of the family Brassicaceae by transforming said member with a vector containing a cDNA sequence encoding metallothionein;
    testing said transformed member for expression of said metallothionein;
    incubating said transformed member in the presence of a lead or chromium solution for time and under conditions sufficient for said transformed member to accumulate lead or chromium into shoots and roots thereof;
    measuring lead or chromium accumulating potential of said transformed member;
    comparing lead or chromium accumulating potential of said transformed member to lead or chromium accumulating potential of another transformed member of the family Brassicaceae;
    identifying which of said transformed members of the family Brassicaceae shows highest lead or chromium accumulating potential;
    introducing said transformed member showing highest lead or chromium accumulating potential into lead or chromium-containing soil under conditions sufficient for said transformed member to accumulate an amount of lead or chromium from said soil.

11. The method of claim 9, wherein the step of altering comprises transforming at least one crop member of the family Brassicaceae.

12. The method of claim 9, wherein the step of altering comprises transforming at least one crop-related member of the family Brassicaceae.

13. The method of claim 9, further comprising harvesting said at least one transformed member from said environment.

14. The method of claim 10, wherein the crop member is selected from the group consisting of *Brassica juncea* and *Brassica oleracea*.

15. The method of claim 11, wherein the crop-related member is selected from the group consisting of *Raphanus sativus* (L.) (radish), *Sinapis alba* (L.) (white mustard). *S. arvensis* (L.), *S. flexuosa* Poiret and *S. pubescens* (L.).

* * * * *

UNITED STATES PATENT AND TRADEMARK OFFICE
CERTIFICATE OF CORRECTION

PATENT NO. : 5,364,451

DATED : November 15, 1994

INVENTOR(S) : Ilya Raskin, Nanda P.B.A. Kumar and Slavik Douchenkov

It is certified that error appears in the above-indentified patent and that said Letters Patent is hereby corrected as shown below:

Column 12, line 30: please delete "men,"; and insert therefor -- member --.

Column 12, line 31: please delete "her".

Column 12, line 66, delete "9" and insert therefor --10--;

Column 13, line 1, delete "9" and insert therefor --10--;

Column 13, line 4, delete "9" and insert therefor --10--;

Column 13, line 7, delete "10" and insert therefor --11--;

Column 14, line 3, delete "11" and insert therefor --12--.

Signed and Sealed this

Twenty-eight Day of February, 1995

Attest:

BRUCE LEHMAN

*Attesting Officer*     *Commissioner of Patents and Trademarks*